(12) United States Patent
Brown et al.

(10) Patent No.: US 6,248,903 B1
(45) Date of Patent: Jun. 19, 2001

(54) PROCESS FOR THE PREPARATION OF METHYL (2S)-2-[(3R)-3-(N-{TERT-BUTYLOXYCARBONYL 9-AMINO)-2-OXOPYRROLIDIN-1-YL]PROPIONATE

(75) Inventors: Richard J Brown; Craig S Harris; Chiu W Leung, all of Macclesfield; Ian Patel, Hallen, all of (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/674,085
(22) PCT Filed: Apr. 27, 1999
(86) PCT No.: PCT/GB99/01307
   § 371 Date: Oct. 26, 2000
   § 102(e) Date: Oct. 26, 2000
(87) PCT Pub. No.: WO99/55669
   PCT Pub. Date: Nov. 4, 1999

(30) Foreign Application Priority Data

Apr. 29, 1998 (GB) ................................................ 9809021

(51) Int. Cl.⁷ ........................ C07D 207/12; C07C 229/00
(52) U.S. Cl. ............................................. 548/550; 560/48
(58) Field of Search .............................. 548/550; 560/148

(56) References Cited

U.S. PATENT DOCUMENTS

| 3,723,534 | 3/1973 | Ratts . | |
| 6,087,336 | 7/2000 | Edwards et al. | 514/14 |

FOREIGN PATENT DOCUMENTS

| 0 026 640 | 4/1981 | (EP) . |
| WO 97/16425 | 5/1997 | (WO) . |
| WO 97/31023 | 8/1997 | (WO) . |
| WO 97/46578 | 12/1997 | (WO) . |
| WO 98/23644 | 6/1998 | (WO) . |

OTHER PUBLICATIONS

Louis F. Fieser et Mary Fieser "reagents for Organic synthesis" 1967. Wiley–Interscience, USA XP002117637, p. 1232, paragraph 3.

Mary Fieser et Louis Fieser: "reagents for Organic Synthesis" 1969, Wiley–Interscience, USA XP002117638, p. 430, paragraph 2–p. 431.

*Primary Examiner*—Deborah C. Lambkin
*Assistant Examiner*—Andrea M D'Souza
(74) *Attorney, Agent, or Firm*—Pillsbury Winthrop LLP

(57) ABSTRACT

The invention concerns a novel chemical process for the manufacture of methyl (2S)-2-[3R)-3-(N-[tert-butyloxycarbonyl]amino)-2-oxopyrrolidin-1-yl]propionate.

11 Claims, No Drawings

PROCESS FOR THE PREPARATION OF METHYL (2S)-2-[(3R)-3-(N-{TERT-BUTYLOXYCARBONYL 9-AMINO)-2-OXOPYRROLIDIN-1-YL]PROPIONATE

This application is a 371 PCT/GB99/01307 Apr. 27, 1999.

The invention concerns a novel chemical process, and more particularly, it concerns a novel chemical process for the manufacture of methyl (2S)-2-[(3R)-3-(-[tert-butyloxycarbonyl]-amino)-2-oxopyrrolidin-1 -yl]propionate of the formula I Formula I

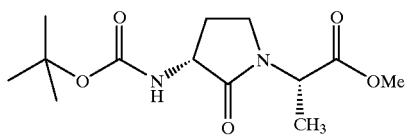

which, for example, is useful in the manufacture of compounds disclosed in International Patent Application, Publication No. WO 97/31023 possessing pharmacologically useful properties for use in treating autoimmune diseases or medical conditions, such as rheumatoid arthritis and other MHC Class II dependent T-cell mediated diseases.

The compound of formula I has previously been prepared by the method disclosed in Example 1 of WO 97/31023. In this method the compound of formula II Formula II

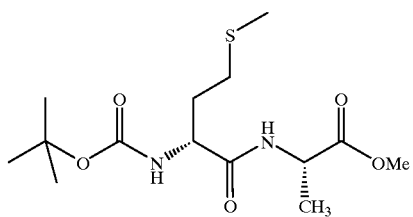

which may be named as Boc-(D)-Met-(L)-Ala-OMe, is methylated using a large excess (about 10 equivalents) of methyl iodide in a mixture of N,N-dimethylformamide (DMF) and dichloromethane, followed by removal of excess methyl iodide and cyclisation of the sulfonium salt formed, using sodium hydride, to form the lactam ring. The product is purified after work-up by chromatography.

There are several disadvantages with carrying out this known process on a large scale. For example, one disadvantage is the use of a large excess of methyl iodide. This results in the production of undesired by-products and is environmentally undesirable. A further disadvantage, for example, is that the alkylation step and the cyclisation step cannot be telescoped together without prior removal of the excess methyl iodide. Unless all the methyl iodide is removed before cyclisation, under the strongly basic conditions used methylation of the amide nitrogen takes place. Further disadvantages for large scale manufacture are the use of DMF as solvent and its removal, and the use of chromatography to purify the product. Also the reaction of methyl iodide with the compound of formula I is reversible and in removing excess methyl iodide from the reaction mixture the product partially reverts to starting material, which effect is enhanced on increasing scale. Such disadvantages make the process unattractive for operation on a commercial scale.

A process has now been discovered for the manufacture of the compound of formula I from Boc-(D)-Met-(L)-Ala-OMe which overcomes one or more of the problems encountered with the known process.

According to the invention, there is provided a process for the manufacture of methyl (2S)-2-[(3R)-3-(N-[tert-butyloxycarbonyl]amino)-2-oxopyrrolidin-1-yl]propionate (Formula I) which comprises (1) methylation of the compound of formula II using trimethyloxonium tetrafluoroborate in a suitable solvent; followed by (2) cyclisation under basic conditions.

In Step (1), a particular solvent which may be employed includes, for example, an inert solvent such as dichloromethane, acetonitrile, tetrahydrofuran or sulpholane, or a mixture thereof. Of these, a preferred solvent is dichloromethane or acetonitrile, especially dichloromethane. Preferably 0.95 to 1.3 equivalents, more preferably 1.0 to 1.25 equivalents (such as 1.13 to 1.23 equivalents), of trimethyloxonium tetrafluoroborate per equivalent of compound of formula II are used in the reaction. Using less than 0.95 equivalents of trimethyloxonium tetrafluoroborate results in significant amounts of unreacted starting material and using a large excess of trimethyloxonium tetrafluoroborate significantly inhibits the subsequent cyclisation step when steps (1) and (2) are telescoped. Most preferably 1.17 equivalents of trimethyloxonium tetrafluoroborate is used. Preferably the addition of the trimethyloxonium tetrafluoroborate is carried out at a temperature in the range −40° C. to ambient temperature, for example 40° C. to +20° C. and conveniently 10 to +10° C., such as 5 to +5° C. The reaction mixture may then conveniently be allowed to proceed to completion at or about ambient temperature, for example, +10° C. to +30° C.

It will be appreciated that the intermediate formed in step (1) is the sulfonium salt of the formula III;

Formula III

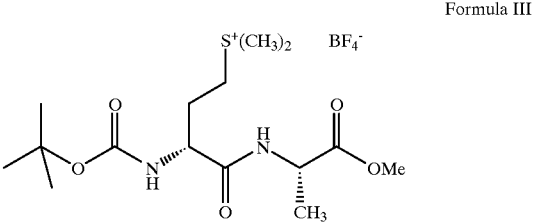

and that this compound is a further aspect of the present invention. In Step (2), a particular base which can be employed includes, for example, an alkali metal alkoxide (such as potassium tert-butoxide, lithium tert-butoxide, sodium tert-butoxide or sodium methoxide), an alkali metal hydride (such as sodium hydride), an alkali metal dialkylamide (such as lithium di-isopropylamide) or an alkyl lithium (such as n-butyl lithium). A preferred base includes, for example, potassium tert-butoxide. Conveniently, 0.8 to 1.1 equivalents (for example 0.85 to 1.05 equivalents, and more especially 0.9 to 1.0 equivalents) of such a base per equivalent of compound of formula II are used, and preferably about 0.94 equivalents (to minimise epimerisation). When such bases are used in Step (2), the reaction is preferably carried out at low temperature, for example −50° C. to 0° C., such as in the range 40° C. to −20° C., and preferably at or about −40° C., such as −50° C. to −30° C.

Surprisingly it has also been found that an alkali metal carbonate, such as sodium or potassium carbonate, especially an alkali metal carbonate in a form having a high surface area, such as powdered anhydrous potassium carbonate (for example 325 mesh size), can be used as the base in Step (2). Furthermore excess of such a carbonate base may be used and the reaction can be carried out satisfactorily at temperatures between ambient temperature and +90° C. for example 20 to 80° C. Preferably 1 to 4 equivalents of such a base per equivalent of compound of formula II are used, especially 2 to 4 equivalents, for example 3 equivalents. Advantages associated with the use of such a carbonate base include, for example, that it is more convenient to use on a large scale, low temperatures do not have to be employed to restrict epimerisation as with a strong base, and the reaction can be carried out at higher concentrations. A preferred aspect of the present invention is therefore the use of such a carbonate base in Step 2 It will be appreciated that other inorganic bases, or mixtures of such bases, having a basicity similar to that of an alkali metal carbonate may also be used in the reaction, preferably in a finely divided form.

A suitable solvent for use in Step (2) includes, for example, any of those suitable for carrying out Step (1), or a mixture thereof. A preferred solvent includes, for example, acetonitrile and dichloromethane, especially the latter. The reaction is generally carried out for 6 to 18 hours, such as about 12 hours. When anhydrous potassium carbonate in dichloromethane is used, it is preferable to carry out Step 2 at the refluxing temperature of dichloromethane. Similarly, Step 2 may be carried out, for example, in refluxing THF, acetonitrile or at 80° C. in sulpholane.

An especially preferred aspect of the present invention comprises a process which comprises (1) methylation of a compound of formula II using 0.95 to 1.05 equivalents of trimethyloxonium tetrafluoroborate per equivalent of compound of formula II, followed by (2) cyclisation under basic conditions using an alkali metal carbonate (preferably anhydrous potassium carbonate).

In a further preferred aspect of the invention, Steps (1) and (2) are telescoped, without prior isolation of the sulphonium salt formed in Step (1). This is particularly advantageous for large scale manufacture. A telescoped procedure using a carbonate base in Step (2) is especially preferred.

The reaction may be worked up by cooling, addition of water, filtration, separation of the organic phase, washing the organic phase with water and removal of volatile material by distillation. The product may be crystallised from a suitable solvent, such as a mixture of dichloromethane and isohexane, tetrahydrofuran and Essochem Solvent 30, an ester such as ethyl, propyl or butyl acetate, or preferably a mixture of n-butyl acetate and isohexane. Alternatively the organic phase, after washing, may be concentrated and then diluted with a suitable solvent or solvents to induce crystallisation, for example as described in the Examples.

The starting material of formula II may be obtained by the procedure described in WO 97/31023. Alternatively the compound of formula II may be obtained by (A) protection of the amino group of (D)-methionine with a butyloxycarbonyl group to give Boc-(D)-methionine; followed by (B) coupling of Boc-(D-methionine with (L)-alanine methyl ester to form Boc-(D)-Met-(L)-Ala-OMe.

Accordingly a further aspect of the invention is a process for preparing the compound of formula I which comprises carrying out Steps (A) and (B), followed by carrying out Steps (1) and (2) described above.

Step (A) may be carried out using a reagent for tert-butoxycarbonylation. such as di-tert-butyl dicarbonate, under basic conditions, for example using excess aqueous sodium hydroxide in tert-butanol. The reaction may be carried out at a temperature in the range −10° C. to +25° C. and conveniently at or about ambient temperature. Preferably the reagent for tert-butoxycarbonylation is added at 0 to 5° C.

Step (B) may be carried out using standard coupling conditions well known in the synthesis of peptides, for example, as described in WO 97/31023 and in the Examples hereinafter.

Preferably Steps (A), (B), (1) and (2) are telescoped together, that is they are carried out without isolation and purification of the intermediates formed, as described in the Examples hereinafter. In this case preferably 0.95 to 1.05 equivalents (more preferably 1 equivalent) of trimethyloxonium tetrafluoroborate per equivalent of Boc-(D)-methionine are used, although it will be appreciated that any of the particular or preferred features of Steps (1) and (2) referred to herein also apply to this 4-step process. Benefits of the telescoped procedure are, for example, that it avoids the problems associated with the use of a large excess of methyl iodide, it reduces the number of evaporation and purification steps required, and the overall yield based on the amount of (D)-methionine used is significantly improved. Additionally, use of potassium carbonate as base in Step (2) is particularly advantageous.

The invention will now be illustrated by the following non-limiting Examples in which, unless otherwise stated:

(i) operations were carried out at room temperature, that is in the range 18–26° C.;

(ii) $^1$H NMR spectra were determined using tetramethysilane (TMS) as an internal standard, and are expressed as chemical shifts (delta values) in parts per million relative to TMS using conventional abbreviations for designation of major peaks: s, singlet; m, multiplet; t, triplet; b, broad; d, doublet.

EXAMPLE 1

Boc-(D)-Met-(L)-Ala-OMe (67.0 g; estimated to contain 0.17 mol)) is dissolved in acetonitrile (500 ml), cooled to 0–5° C. and trimethyloxonium tetrafluoroborate (29.6 g; 0.2 mol)) is added in portions keeping the temperature at 0–5° C. The mixture is allowed to warm to 20° C. over 30 minutes and is stirred for a further 90 minutes. Further acetonitrile (2000 ml) is added, the mixture is cooled to −40° C. and a solution of 1M potassium tert-butoxide in tetrahydrofuran (160 ml) is added over 60 minutes, maintaining the temperature of the reaction mixture at −40° C. The mixture is allowed to warm to 20° C. for 16 hours. The mixture is evaporated to dryness at 40° C. under reduced pressure and the resulting oil is partitioned between brine (600 ml) and dichloromethane (400 ml). The organic phase is separated and the aqueous phase is extracted with dichloromethane (200 ml). The combined organic phases are washed with water (200 ml) and isohexane (1600 ml) is added. The solution is concentrated by distillation at atmospheric pressure to a head temperature of 53° C. to remove dichloromethane. The remaining solution is cooled to 40° C. to initiate crystallisation and further isohexane (200 ml) is added. The mixture is heated to reflux and is maintained at reflux for 2 hours. The mixture is then allowed to cool to ambient temperature. The suspended crystalline product is collected by filtration, washed with cold isohexane and dried at 50° C. in a vacuum oven. There is thus obtained methyl (2S)-2-[(3R)-3-(N-[tert-butyloxycarbonyl]amino)-2-oxopyrrolidin-1-yl)propionate (28.4 g); $^1$H NMR (200MHz, CDCl$_3$): 1.4 (s,9H), 1.4 (d,3H), 1.8 (m,1H), 2.6 (m,1H), 3.4 (m,2H), 3.7(s,3H), 4.2(m,1H), 4.9(q,1H), 5.2 (bs, 1H).

The starting material is obtained as follows:

Boc-(D)-methionine (50.0 g) is dissolved in dichloromethane (200 ml) and 1-hydroxybenzo-triazole hydrate (29.7 g) and (L)-alanine methyl ester hydrochloride (31.0 g) is added. The mixture is cooled to 0° C. and 1-(3-dimethylaminopropyl)-3-ethylcarbodiimide hydrochloride (43.0 g) is added in portions, maintaining the temperature of the mixture at 0–5° C. N-Methylmorpholine (42.2 g) is then added over 30 minutes, maintaining the temperature of the mixture at 0–5° C. The mixture is then stirred at 0° C. for 5 hours. The reaction mixture is washed successively with water (2×100 ml), 10% aqueous citric acid solution (100 ml), saturated aqueous sodium bicarbonate solution (100 ml), water (100 ml) and evaporated to dryness at 40° C. under reduced pressure to give Boc-(D)-Met-(L)-Ala-OMe (67.0 g estimated to contain 0.17 mol) as an oil.

EXAMPLE 2 (telescoped process)

Sodium hydroxide solution (1.88M; 150 ml) was added to (D)-methionine (25.0 g; 0.166 mol) and tert-butanol (100 ml) was added. The mixture was cooled to 0–5° C. and di-tert-butyl dicarbonate (41.1 g) added in one portion. The reaction mixture was warmed to 20° C. and stirred for 4 hours. The mixture was cooled to 0–5° C. and 2M aqueous citric acid solution (128 ml) was added, maintaining the temperature below 5° C. Dichloromethane (250 ml) was added and the mixture stirred at 20° C. for 15 minutes. The upper aqueous phase was separated and the organic phase retained. The aqueous phase was extracted with dichloromethane (125 ml) and the extract was combined with the retained organic phase. The combined organic phase was washed with water (250 ml) and distilled at atmospheric pressure until a volume of 250 ml remained. The solution (which contains Boc-(D)-methionine) was cooled to 0–5° C. and (L)-alanine methyl ester hydrochloride (25.7 g), 1-hydroxybenzotriazole hydrate (24.6 g), 1-(3-dimethylaminopropyl)-3-ethylcarbodiimide hydrochloride (35.6 g) and N-methyl-morpholine (35.6 g) was added maintaining the temperature of the mixture below 5° C. The mixture was then warmed to 20° C. and stirred at this temperature for 5 hours. The mixture was cooled to 0–5° C. and water (100 ml) was added, maintaining the temperature below 5° C., and the mixture was stirred for 15 minutes. The organic phase was separated and washed successively with water (150 ml), 2M aqueous citric acid solution (100 ml), 20% aqueous sodium bicarbonate solution (100 ml) and brine (100 ml). Dichloromethane (450 ml) was added to the organic phase and the mixture distilled at atmospheric pressure until 100 ml of distillate was collected. The mixture (which contains Boc-(D)-Met-(L)-Ala-OMe) was cooled to 0–5° C. and trimethyloxonium tetrafluoroborate (25.1 g; 0.166 mol) was added in one portion keeping the temperature at 0–5° C. The mixture was allowed to warm to 20° C. over 30 minutes and then stirred for a further 4 hours. Powdered potassium carbonate (325 mesh; 71.9 g) was added and the mixture was refluxed for 12 hours. The mixture was cooled to 0–5° C. and water (300 ml) was added. The mixture was stirred for 15 minutes at 20° C. and filtered through a sinter funnel (porosity 3). The lower organic phase of the filtrate was separated and washed with water (300 ml). The solution was distilled at atmospheric pressure until 320 ml of distillate was collected and n-butyl acetate (200 ml) was added. The solution was concentrated at 70–75° C. under reduced pressure until 80 ml of concentrate remained. The concentrate was cooled to 40° C. and isohexane (80 ml) was added. The mixture was cooled to 20° C., then heated to 40° C. and further isohexane (320 ml) added slowly over 1 hour. The mixture was stirred a further 30 minutes at 40° C. and then cooled to 0–5° C. and stirred for 1 hour. The suspended crystalline solid was collected by filtration, washed with cold isohexane (2×50 ml), and dried at 50° C. in a vacuum oven for 8 hours. There was thus obtained methyl (2S)-2-[(3R)-3-(N-[tert-butyloxycarbonyl] amino)2-oxopyrrolidin1-yl]propionate (36.5 g; 76% yield); NMR as for Example 1.

What we claim is:

1. A process for the manufacture of methyl (2S)-2-[(3R)-3-(N-[tert-butyloxycarbonyl]amino)-2-oxopyrrolidin-1-yl] propionate of the formula I:

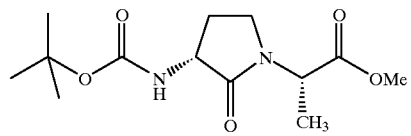

which comprises (1) methylation of the compound of formula II

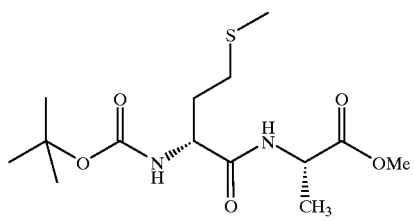

using trimethyloxonium tetrafluoroborate in a suitable solvent; followed by (2) cyclisation under basic conditions.

2. A process as claimed in claim 1 wherein the solvent used in step (1) comprises dichloromethane or acetonitrile and in step (2) comprises dichloromethane, acetonitrile, tetrahydrofuran or sulpholane.

3. A process as claimed in claim 1 or 2 wherein 0.95 to 1.3 equivalents of trimethyloxonium tetrafluoroborate per equivalent of the compound of formula II is used.

4. A process as claimed in claim 1 or 2 wherein in step (2) the base used is an alkali metal alkoxide, an alkali metal hydride, an alkali metal dialkylamide or an alkyl lithium.

5. A process as claimed in claim 1 or 2 wherein in step (2) the base used is an alkali metal carbonate.

6. A process as claimed in claim 5 wherein step (2) is carried out at a temperature between ambient temperature and 90° C.

7. A process as claimed in claim 5 wherein 1 to 4 equivalents of powdered potassium carbonate are used.

8. A process as claimed in claim 1 or 2 wherein the compound of formula I is isolated by crystallisation from a solvent mixture comprising n-butyl acetate and isohexane or dichloromethane and isohexane.

9. A process for the manufacture of the compound of formula I which comprises the steps of:

(i) protection of the amino group of (D)-methionine with a butyloxycarbonyl group to give Boc-(D)-methionine;

(ii) coupling of Boc-(D)-methionine with (L)-alanine methyl ester to form Boc-(D)-Met-(L)-Ala-OMe;

(iii) methylation of Boc-(D)-Met-(L)-Ala-OMe with trimethyloxonium tetrafluoroborate in a suitable solvent; and (iv) cyclisation under basic conditions.

10. A process as claimed in claim 1 or 2 in which all steps are telescoped.

11. The compound

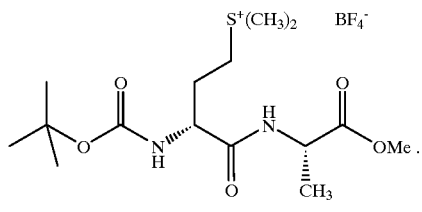

* * * * *